(12) United States Patent
Retsina et al.

(10) Patent No.: US 9,085,494 B2
(45) Date of Patent: *Jul. 21, 2015

(54) PROCESSES FOR PRODUCING LOW-ASH BIOMASS FOR COMBUSTION OR PELLETS

(71) Applicant: API Intellectual Property Holdings, LLC, Atlanta, GA (US)

(72) Inventors: Theodora Retsina, Atlanta, GA (US); Vesa Pylkkanen, Atlanta, GA (US)

(73) Assignee: API Intellectual Property Holdings, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/173,239

(22) Filed: Feb. 5, 2014

(65) Prior Publication Data

US 2014/0154759 A1 Jun. 5, 2014

Related U.S. Application Data

(63) Continuation of application No. 13/829,237, filed on Mar. 14, 2013, now Pat. No. 8,685,685.

(60) Provisional application No. 61/612,451, filed on Mar. 19, 2012.

(51) Int. Cl.

| C12P 7/10 | (2006.01) |
|---|---|
| C05F 17/00 | (2006.01) |
| C08B 1/00 | (2006.01) |
| C12P 19/14 | (2006.01) |
| C10L 5/44 | (2006.01) |
| C08H 8/00 | (2010.01) |
| C12P 7/06 | (2006.01) |
| C12P 7/16 | (2006.01) |
| C12P 7/54 | (2006.01) |
| C12P 7/56 | (2006.01) |
| C13K 1/02 | (2006.01) |
| F23G 7/12 | (2006.01) |

(52) U.S. Cl.
CPC ............ *C05F 17/00* (2013.01); *C08B 1/003* (2013.01); *C08H 8/00* (2013.01); *C10L 5/44* (2013.01); *C12P 7/06* (2013.01); *C12P 7/10* (2013.01); *C12P 7/16* (2013.01); *C12P 7/54* (2013.01); *C12P 7/56* (2013.01); *C12P 19/14* (2013.01); *C13K 1/02* (2013.01); *F23G 7/12* (2013.01); *C10L 2290/08* (2013.01); *C10L 2290/10* (2013.01); *C10L 2290/544* (2013.01); *C12P 2201/00* (2013.01); *Y02E 50/10* (2013.01); *Y02E 50/16* (2013.01); *Y02E 50/17* (2013.01); *Y02E 50/30* (2013.01); *Y02W 30/43* (2015.05)

(58) Field of Classification Search
USPC ........................ 435/165, 140; 127/37
See application file for complete search history.

(56) References Cited

U.S. PATENT DOCUMENTS

| 5,328,562 | A | 7/1994 | Rafferty et al. | |
|---|---|---|---|---|
| 8,518,672 | B2 * | 8/2013 | Retsina et al. | 435/105 |
| 8,685,685 | B2 * | 4/2014 | Retsina et al. | 435/165 |
| 8,906,657 | B2 * | 12/2014 | Retsina et al. | 435/165 |
| 2010/0330633 | A1 | 12/2010 | Walther et al. | |
| 2012/0009632 | A1 | 1/2012 | Retsina et al. | |
| 2013/0104880 | A1 * | 5/2013 | Stuart | 127/37 |

FOREIGN PATENT DOCUMENTS

WO 2011020082 A1 2/2011

OTHER PUBLICATIONS

International Preliminary Report on Patentability for PCT/US2013/032016, dated Sep. 23, 2014.
Zhu and Pan, "Woody biomass pretreatment for cellulosic ethanol production: Technology and energy consumption evaluation," Bioresource Technology 101 (2010) 4992-5002.
Chum et al., "Evaluation of pretreatments of biomass for enzymatic hydrolysis of cellulose," NREL report 231-2183, Oct. 1985, retrieved at www.nrel.gov/docs/legosti/old/2183.pdf.
Biswas et al., "Steam pretreatment of Salix to upgrade biomass fuel for wood pellet production," Fuel Processing Technology 92 (2011) 1711-1717.
Laser et al., "A comparison of liquid hot water and steam pretreatments of sugar cane bagasse for bioconversion to ethanol," Bioresource Technology 81 !2002) 33-44.

* cited by examiner

*Primary Examiner* — Ralph Gitomer
(74) *Attorney, Agent, or Firm* — Ryan P. O'Connor

(57) ABSTRACT

This invention provides processes and apparatus to convert biomass, including wood and agricultural residues, into low-ash biomass pellets for combustion, alone or in combination with another solid fuel. Some embodiments provide processes for producing low-ash biomass from cellulosic biomass, comprising providing an aqueous extraction solution with acetic acid; extracting the feedstock to produce an extract liquor containing soluble ash, hemicellulosic oligomers, acetic acid, dissolved lignin, and cellulose-rich solids; dewatering and drying the cellulose-rich, lignin-rich solids to produce a low-ash biomass; hydrolyzing the hemicellulosic oligomers to produce hemicellulosic sugars, wherein additional acetic acid is generated; removing a vapor stream comprising vaporized acetic acid from the extract; and recycling the vapor or its condensate to provide some starting acetic acid for the extraction solution. The disclosed processes can produce clean power from biomass. Co-products may include fermentable sugars, fermentation products such as ethanol, fertilizers, and lignin.

18 Claims, 1 Drawing Sheet

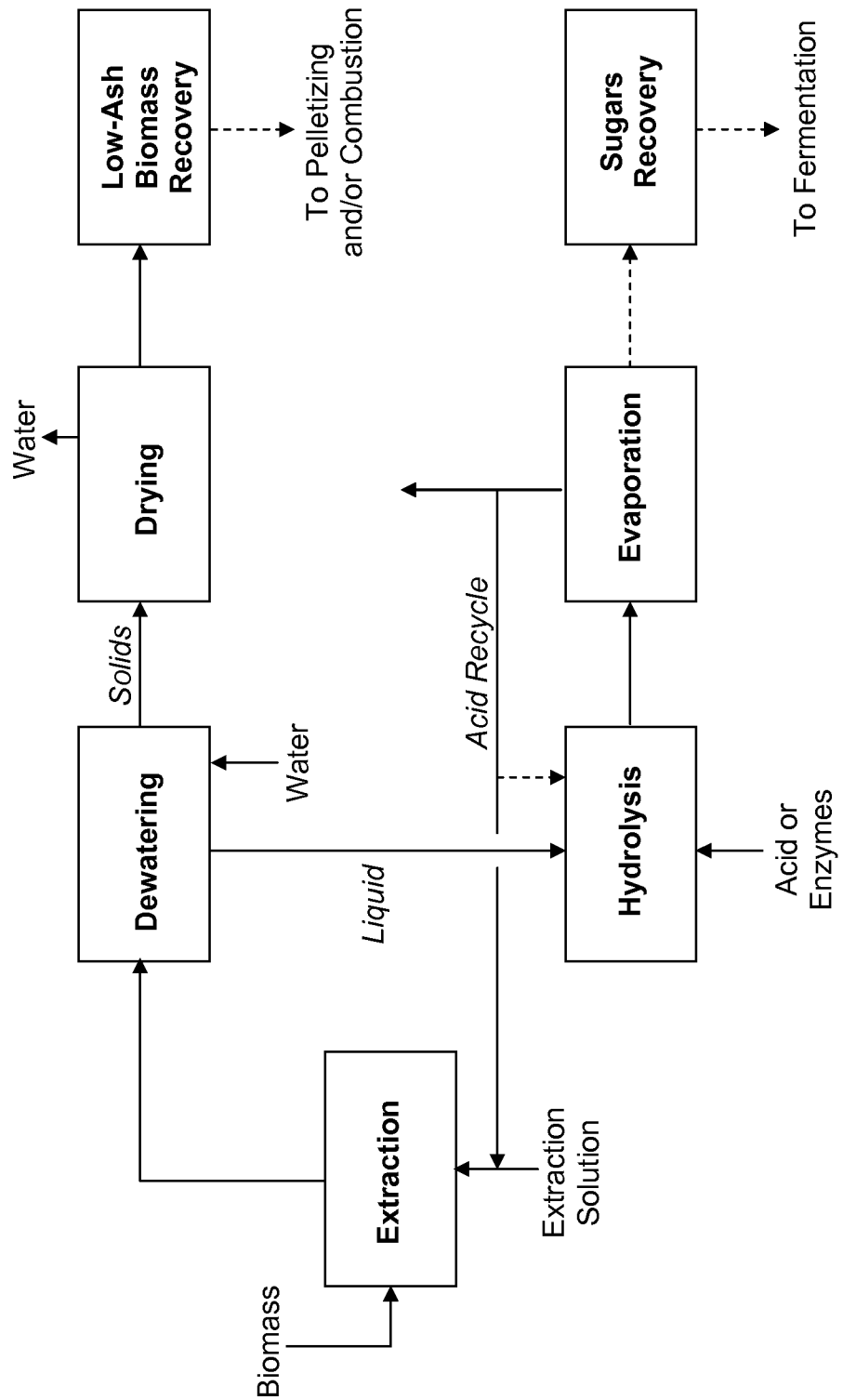

PROCESSES FOR PRODUCING LOW-ASH BIOMASS FOR COMBUSTION OR PELLETS

PRIORITY DATA

This patent application is a continuation patent application of U.S. Pat. No. 8,685,685, issued on Apr. 1, 2014, which claims priority to U.S. Provisional Patent App. No. 61/612,451, filed Mar. 19, 2012, each of which is hereby incorporated by reference herein.

STATEMENT REGARDING FEDERALLY SPONSORED RESEARCH OR DEVELOPMENT

This invention was made with Government support under Contract No. DE-EE0002868. The Government has certain rights in this invention.

FIELD OF THE INVENTION

The present invention generally relates to processes for preparing low-ash biomass for combustion, while also recovering fermentable sugars from the biomass.

BACKGROUND OF THE INVENTION

Wood and biomass burning is making a comeback after over a century of domination by coal, petroleum, and natural gas for power generation. The availability of energy-dense fossil fuels and efficient transportation networks made centralized power production the technology of choice. In the 21st century, biomass heat and power plants and district heating are enjoying a renaissance. This popularity is driven in part by the carbon-neutral nature of most biomass (i.e., no net $CO_2$ emissions). The rising cost of fossil fuels and incentives for switching drive consumer decisions toward renewable energy. Also, renewable-energy portfolio mandates require that utilities construct renewable power plants.

One option is converting existing coal-fired power plants into plants that can utilize biomass, or be co-fired with biomass. The co-firing is limited in part because of undesired changes in the resulting ash composition, such as high quantities of alkali metals. Biomass pellets are also increasingly used in uncontrolled domestic heat generators. European Committee for Standardization (www.cen.eu), Technical Committee guidelines for domestic heating pellets recommends ash content less than 0.7%, limiting materials that can be used.

One challenge to combusting biomass is its high moisture content. Living and freshly cut biomass typically contains moisture between 40% and 60%. In loose storage, the biomass dryness can reach air-dry moisture of about 10%. This drying of wood is slow, typically requiring at least a full summer season. This necessitates double handling and increases procurement cost.

It can be advantageous to first pelletize biomass, to increase energy efficiencies of boilers. Pelletizing processes can drive moisture out of the biomass, by using part of the biomass energy, waste heat, or a fossil fuel. The final moisture from pelletizing is typically 5-7%, which is similar to moisture of coal. Boiler efficiencies increase approximately half a percent with each percentage removal of moisture.

In biomass, cellulose and hemicellulose each have about half of the calorific heat value of coal, because of high oxygen content of polymeric sugar constituents. Lignin has a similar calorific heat value to coal, but sulfur is nearly absent. The combined energy content of biomass is typically 8,000-9,000 Btu/lb, as compared to 10,000-14,000 Btu/lb in coal. Because of high oxygen content and moisture in biomass, the boiler efficiency for biomass firing typically ranges from 50-65%. A large portion of heat generated in combustion escapes as steam through the stack. Therefore, converting coal-burning boilers to biomass firing may reduce boiler capacity by as much as 60%.

Feeding irregularly shaped biomass also represents a challenge. Pelletizing can produce uniformly sized material that does not bridge or lodge easily in a storage silo. On the other hand, the pelletized material can absorb moisture, if stored loosely outdoors.

Another obstacle is presented by the ash in the biomass. Hardwood and softwood stem and forest trimmings contain 0.4% to 0.8% ash that is rich in calcium and potassium. Other biomass materials including pulp and paper sludge, paper waste, recycled paper and construction waste, can contain up to 30% ash. Such ash includes minerals in plant capillaries, dirt on the surface, and coating in the paper. The wood exposed to salt water contains elevated levels of sodium and chlorides.

Agricultural residues of annual plants, such as corn stover, corn fiber, wheat straw, sugarcane bagasse, rice straw, oat straw, barley straw, miscanthus, and energy cane can contain up to 10% or more ash that is rich in silica, potassium, and chlorine. The agricultural residue material is very lean in sulfur, typically less than 0.1%, versus coal sulfur content of 0.5-7.5%. Significant minerals in these annual agricultural residues include potassium, sodium, silica, calcium, and corrosive halogens such as chlorides.

Upon combustion at high temperatures, metals and halogens volatilize to aerosols and carry over from the boiler with flue gas. The cooling of fly ash creates microscopic particles that are found to cause respiratory illnesses. Flue-gas treatment for particulate removal includes cyclones, scrubbers, and electrostatic precipitators (ESP). These environmental controls in the central power plant are expensive and, in domestic applications, tend to be cost-prohibitive. Recent Maximum Achievable Control Technology (MACT) legislation by the U.S. EPA seeks to control particulate emissions from large biomass power plants. Other minerals such as calcium and silica remain in the bottom of the boiler and have tendency to form clinkers and to scale (slag) in the boiler tubes. Alkaline chloride salts can cause corrosion of the boiler tubes.

What are needed are processes and apparatus to prepare biomass, including wood and agricultural residues, into clean, low-ash biomass for improved combustion, with or without first pelletizing the biomass. The low-ash biomass should be capable of being fired alone or in combination with another solid fuel. It would be desirable for these processes to also have good potential to recover various co-products, such as fermentable sugars, fertilizers, and lignin.

SUMMARY OF THE INVENTION

The present invention addresses the aforementioned needs in the art.

In some variations, the invention provides a process for producing fermentable hemicellulosic sugars and low-ash biomass from cellulosic biomass, the process comprising:

(a) providing a feedstock comprising cellulosic biomass;

(b) providing an extraction solution comprising steam and/or hot water, and starting acetic acid;

(c) treating the feedstock with the extraction solution under effective extraction conditions to produce an extract liquor containing soluble ash, hemicellulosic oligomers, acetic acid, dissolved lignin, and cellulose-rich solids;

(d) separating at least a portion of the cellulose-rich solids from the extract liquor, to produce dewatered solids containing cellulose and lignin;

(e) hydrolyzing the hemicellulosic oligomers contained in the extract liquor, under effective hydrolysis conditions, to produce fermentable hemicellulosic sugars, wherein the effective hydrolysis conditions release acetyl groups to generate additional acetic acid;

(f) removing a vapor stream comprising water and vaporized acetic acid from the extract liquor in at least one evaporation stage at a pH of 4.8 or less, to produce a concentrated extract liquor comprising the fermentable hemicellulosic sugars;

(g) recycling at least a portion of the vapor stream from step (f), or a condensed form thereof, back to step (b) to provide at least some of the starting acetic acid for the extraction solution and to provide heat for step (c);

(h) optionally recovering the fermentable hemicellulosic sugars; and (i) drying the dewatered solids to produce the low-ash biomass.

The feedstock may be selected from hardwood, softwood, agricultural residues, forest residues, industrial wastes, consumer wastes, or combinations thereof. In various embodiments, the feedstock is selected from the group consisting of corn stover, corn fiber, wheat straw, sugarcane bagasse, rice straw, oat straw, barley straw, miscanthus, energy cane, forest trimmings, pulp and paper waste, paper waste, wood waste, and combinations thereof In some embodiments, the extraction solution comprises steam in saturated, superheated, or supersaturated form. In certain embodiments, the extraction solution comprises hot water.

The extraction solution may be entirely derived from the vapor stream from step (f), in some embodiments. The extraction solution may include evaporator condensate from step (f). Various mixtures of recycled and fresh extraction solution are possible.

In some embodiments, the extraction solution contains from about 0.01 wt % to about 10 wt % acetic acid, such as from about 0.05 wt % to about 4 wt % acetic acid. The extraction solution may further contain up to about 2 wt % formic acid and other acids. In certain embodiments, the extraction solution further contains sulfur dioxide, sulfurous acid, sulfuric acid, or any combination thereof.

The soluble ash in the extract liquor produced in step (c) may include halogens, such as chlorine or chlorides. The soluble ash may include silica or silicates. Also, the soluble ash may include metals or derivatives thereof.

In some embodiments, step (d) includes washing the extract liquor from the cellulose-rich solids using an aqueous wash solution, and pressing the cellulose-rich solids to produce the dewatered cellulose-rich solids.

Between steps (d) and (e), the extract liquor may be concentrated in an intermediate evaporation stage at a pH of 4.8 or less (separate from the later evaporation stage(s) in step (f)). The process may further comprise recycling at least a portion of vaporized acetic acid derived from the intermediate evaporation stage back to the extraction solution, when an intermediate evaporation stage is present.

Effective hydrolysis conditions in step (e) may include hydrolysis in the presence of a strong acid, such as sulfuric acid. In some embodiments, hydrolysis conditions in step (e) include hydrolysis in the presence of heat and acetic acid. Alternatively, enzymes (e.g., hemicellulase enzymes) may be employed for the hydrolysis in step (e).

Step (f) may be conducted such that the concentrated extract liquor includes at least 10%, 20 wt %, 30 wt %, 40 wt %, or more solids. In some embodiments, at least one evaporation stage in step (f) is controlled at a pH selected from about 3 to 4.8.

The process may further comprise removing at least a portion of the dissolved lignin from the extract liquor, the concentrated extract liquor, or both of these, to generate recovered lignin.

The process may further comprise combusting the low-ash biomass, to produce power. Prior to combustion, pellets may be formed. In some embodiments, the process comprises pelletizing the dewatered cellulose-rich solids, prior to step (i). In these or other embodiments, the low-ash biomass is pelletized to produce biomass pellets. The process may be operated so that the low-ash biomass contains about the same moisture content as contained in the cellulosic biomass, if desired.

Optionally, the process may include co-combusting the recovered lignin with the low-ash biomass, to produce power. The recovered lignin may be combined with the low-ash biomass prior to combustion, or they may be co-fired as separate streams. When recovered lignin is combined with the low-ash biomass for making pellets, the lignin can act as a pellet binder.

The process may further include fermenting the fermentable hemicellulosic sugars to a fermentation product, such as (but by no means limited to) ethanol, 1-butanol, or isobutanol. A purified fermentation product may be produced by distilling the fermentation product, which will also generate a distillation bottoms stream containing residual solids. A bottoms evaporation stage may be used, to produce residual solids.

Part or all of the residual solids may be co-combusted with the low-ash biomass, if desired. Alternatively, or additionally, the process may include recovering the residual solids as a fermentation co-product in solid, liquid, or slurry form. The fermentation co-product may be used as a fertilizer or fertilizer component, since it will typically be rich in potassium, nitrogen, and/or phosphorous.

In certain embodiments, the process further comprises combining, at a pH of about 4.8 to 10 or higher, a portion of the vaporized acetic acid with an alkali oxide, alkali hydroxide, alkali carbonate, and/or alkali bicarbonate, wherein the alkali is selected from the group consisting of potassium, sodium, magnesium, calcium, and combinations thereof, to convert the portion of the vaporized acetic acid to an alkaline acetate. The alkaline acetate may be recovered. If desired, purified acetic acid may be generated from the alkaline acetate.

The low-ash biomass has lower inorganic emissions potential compared to the cellulosic biomass, in preferred embodiments. The reason is that the low-ash biomass will contain lower ash content compared to an otherwise-identical process that does not extract inorganic components from the feedstock prior to combustion. Also, the low-ash biomass will generally have higher energy density compared to an otherwise-identical process that does not extract hemicellulosic sugars from the feedstock prior to combustion.

Preferably, the low-ash biomass has a low enough alkaline content making it acceptable for co-firing with coal in a boiler. In some embodiments, the process further comprises co-combusting the low-ash biomass and coal in a boiler, to produce power, wherein the low-ash biomass may be at least 10%, 20%, 30%, 40%, 50% or more of the fuel that is co-combusted in the boiler.

Preferably, the low-ash biomass has a low enough ash content making it acceptable for burning in a furnace. In some embodiments, the process further comprises combusting the low-ash biomass in a furnace, such as a domestic furnace to produce heat.

Other variations of the invention provide a process for producing fermentable hemicellulosic sugars and biomass pellets from cellulosic biomass, the process comprising:

(a) providing a feedstock comprising cellulosic biomass;

(b) providing an extraction solution comprising steam and/or hot water, and starting acetic acid;

(c) treating the feedstock with the extraction solution under effective extraction conditions to produce an extract liquor containing soluble ash, hemicellulosic oligomers, acetic acid, dissolved lignin, and cellulose-rich solids;

(d) separating at least a portion of the cellulose-rich solids from the extract liquor, to produce dewatered cellulose-rich solids;

(e) hydrolyzing the hemicellulosic oligomers contained in the extract liquor, under effective hydrolysis conditions, to produce fermentable hemicellulosic sugars, wherein the effective hydrolysis conditions release acetyl groups to generate additional acetic acid;

(f) removing a vapor stream comprising water and vaporized acetic acid from the extract liquor in at least one evaporation stage at a pH of 4.8 or less, to produce a concentrated extract liquor comprising the fermentable hemicellulosic sugars;

(g) recycling at least a portion of the vapor stream from step (f), or a condensed form thereof, back to step (b) to provide at least some of the starting acetic acid for the extraction solution and to provide heat for step (c);

(h) optionally recovering the fermentable hemicellulosic sugars;

(i) drying the dewatered cellulose-rich solids, to produce the low-ash biomass; and (j) pelletizing the low-ash biomass, to produce biomass pellets.

In some embodiments, the process further comprises removing at least a portion of the dissolved lignin from the extract liquor and/or from the concentrated extract liquor, to generate recovered lignin. Step (j) may include binding the dewatered cellulose-rich solids with a binder comprising the recovered lignin, to produce the biomass pellets.

Some variations relating to annually renewable cellulosic biomass provide a process for producing fermentable hemicellulosic sugars and power, the process comprising:

(a) providing an annually renewable cellulosic biomass feedstock;

(b) providing an extraction solution comprising steam and/or hot water, and starting acetic acid;

(c) treating the feedstock with the extraction solution under effective extraction conditions to produce an extract liquor containing soluble ash, hemicellulosic oligomers, inorganic components, acetic acid, dissolved lignin, and cellulose-rich solids;

(d) separating at least a portion of the cellulose-rich solids from the extract liquor, to produce dewatered cellulose-rich solids;

(e) hydrolyzing the hemicellulosic oligomers contained in the extract liquor, under effective hydrolysis conditions, to produce fermentable hemicellulosic sugars, wherein the effective hydrolysis conditions release acetyl groups to generate additional acetic acid;

(f) removing a vapor stream comprising water and vaporized acetic acid from the extract liquor in at least one evaporation stage at a pH of 4.8 or less, to produce a concentrated extract liquor comprising the fermentable hemicellulosic sugars;

(g) recycling at least a portion of the vapor stream from step (f), or a condensed form thereof, back to step (b) to provide at least some of the starting acetic acid for the extraction solution and to provide heat for step (c);

(h) optionally recovering the fermentable hemicellulosic sugars; and (i) drying and combusting the dewatered cellulose-rich solids, to produce power.

Other variations relating to annually renewable cellulosic biomass provide a process for producing fermentable hemicellulosic sugars and biomass pellets, the process comprising:

(a) providing an annually renewable cellulosic biomass feedstock;

(b) providing an extraction solution comprising steam and/or hot water, and starting acetic acid;

(c) treating the feedstock with the extraction solution under effective extraction conditions to produce an extract liquor containing hemicellulosic oligomers, inorganic components, acetic acid, dissolved lignin, and cellulose-rich solids;

(d) separating at least a portion of the cellulose-rich solids from the extract liquor, to produce dewatered cellulose-rich solids;

(e) hydrolyzing the hemicellulosic oligomers contained in the extract liquor, under effective hydrolysis conditions, to produce fermentable hemicellulosic sugars, wherein the effective hydrolysis conditions release acetyl groups to generate additional acetic acid;

(f) removing a vapor stream comprising water and vaporized acetic acid from the extract liquor in at least one evaporation stage at a pH of 4.8 or less, to produce a concentrated extract liquor comprising the fermentable hemicellulosic sugars;

(g) recycling at least a portion of the vapor stream from step (f), or a condensed form thereof, back to step (b) to provide at least some of the starting acetic acid for the extraction solution and to provide heat for step (c);

(h) optionally recovering the fermentable hemicellulosic sugars; and (i) pelletizing the dewatered cellulose-rich solids, to produce biomass pellets.

BRIEF DESCRIPTION OF THE FIGURE

FIG. 1 is a simplified block-flow diagram depicting the process of some embodiments of the present invention.

DETAILED DESCRIPTION OF EMBODIMENTS OF THE INVENTION

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

The present invention is premised, at least in part, on the realization that pretreatment of biomass may be optimized to remove water-soluble ash from the biomass, and therefore reduce volatilized mineral ash in the flue gas when the biomass is combusted. In some variations, it has been discovered that acids added before or during biomass pretreatment can increase the extent of mineral release and/or increase the mineral solubility in solution, so that surprisingly high amounts of ash are removed. The extract may be further treated to make fermentable sugars, and optionally fermentation products. In an integrated process, unused solids or other combustible components recovered at any point may be fed to the combustion.

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for illustration purposes only.

In some embodiments, such as the process depicted in FIG. 1, the process starts as biomass is received or reduced to approximately ¼" thickness. In a first step of the process, the biomass chips are fed to a pressurized extraction vessel operating continuously or in batch mode. The chips may be steamed or water-washed to remove dirt and entrained air. The chips are immersed with aqueous liquor or saturated vapor and heated to a temperature between about 100° C. to about 250° C., for example 150° C., 160° C., 170° C., 180° C., 190° C., 200° C., or 210° C. Preferably, the chips are heated to about 180° C. to 210° C. The pressure in the pressurized vessel may be adjusted to maintain the aqueous liquor as a liquid, a vapor, or a combination thereof. Exemplary pressures are about 1 atm to about 30 atm, such as about 3 atm, 5 atm, 10 atm, or 15 atm.

The aqueous liquor may contain acidifying compounds, such as (but not limited to) sulfuric acid, sulfurous acid, sulfur dioxide, acetic acid, formic acid, or oxalic acid, or combinations thereof. The dilute acid concentration can range from 0.01% to 10% as necessary to improve solubility of particular minerals, such as potassium, sodium, or silica. Preferably, the acid concentration is selected from about 0.01% to 4%, such as 0.1%, 0.5%, 1%, 1.5%, 2%, 2.5%, 3%, or 3.5%.

A second step may include depressurization of the extracted chips. The vapor can be used for heating the incoming woodchips or cooking liquor, directly or indirectly. The volatilized organic acids (e.g., acetic acid), which are generated or included in the cooking step, may be recycled back to the cooking A third step may include washing the extracted chips. The washing may be accomplished with water, recycled condensates, recycled permeate, or combination thereof. A liquid biomass extract is produced. A countercurrent configuration may be used to maximize the biomass extract concentration. Washing typically removes most of the dissolved material, including hemicelluloses and minerals. The final consistency of the washing may be increased to 30% or more, preferably to 50% or more, using a mechanical pressing device.

A fourth step may include drying of the extracted material to a desired final moisture. The heat necessary for drying may be derived from combusting part of the starting biomass. Alternatively, or additionally, the heat for drying may be provided by other means, such as a natural gas boiler or other auxiliary fossil fuel, or from a waste heat source. Optionally, drying of the extracted material may be accomplished by pyrolysis, torrefaction (mild pyrolysis), or gasification of the extracted material.

A fifth step may include preparing the biomass for combustion. This step may include grinding, milling, fluidizing, and/or pelletizing the extracted biomass. The biomass may be fed to a boiler in the form of fine powder, loose fiber, pellets, briquettes, or any other suitable form. In some embodiments, pellets of extracted biomass ("biomass pellets") are preferred.

A sixth step is combustion of the biomass, which in some embodiments is in the form of biomass pellets. The biomass pellets are fed to boiler and combusted, preferably with excess air, using well-known combustion apparatus. Boiler bottom may be fixed, moving, or fluidized for the best efficiency. The flue gas is cooled and fly ash is collected into gravity collectors. In some embodiments, the extracted biomass is sufficiently low in ash such that when the extracted biomass is combusted, particulate matter emissions are very low. In certain embodiments, the particulate matter emissions are so low as to avoid the need for any additional cleaning device, and associated control system, in order to meet current emission regulations.

A seventh step may include treatment of the biomass extract to form a hydrolyzate comprising fermentable hemicellulose sugars. In some embodiments, the biomass extract is hydrolyzed using dilute acidic conditions at temperatures between about 100° C. and 190° C., for example about 120° C., 130° C., 140° C., 150° C., 160° C., or 170° C., and preferably from 120° C. to 150° C.

The acid may be selected from sulfuric acid, sulfurous acid, or sulfur dioxide. Alternatively, or additionally, the acid may include formic acid, acetic acid, or oxalic acid from the cooking liquor or recycled from previous hydrolysis. Alternatively, hemicellulase enzymes may used instead of acid hydrolysis. The lignin from this step may be separated and recovered, or recycled to increase the heating value of the pellets, or sent directly to the boiler.

An eighth step may include evaporation of hydrolyzate to remove some or most of the volatile acids. The evaporation may include flashing or stripping to remove sulfur dioxide, if present, prior to removal of volatile acids. The evaporation step is preferably performed below the acetic acid dissociation pH of 4.8, and most preferably a pH selected from about 1 to about 2.5. The dissolved solids are concentrated, such as to about 10% to about 40% to optimize fermentable hemicellulose sugar concentration to a particular microorganism. *Saccharomyces Cerevisiae* fermentation can withstand dissolved solids concentrations of 30-50%, while *Clostridia Acetobutylicum* fermentation is viable at 10-20% concentrations only.

In some embodiments, additional evaporation steps may be employed. These additional evaporation steps may be conducted at different conditions (e.g., temperature, pressure, and pH) relative to the first evaporation step.

In some embodiments, some or all of the organic acids evaporated may be recycled, as vapor or condensate, to the first step (cooking step) and/or third step (washing step) to remove assist in the removal of minerals from the biomass. This recycle of organic acids, such as acetic acid, may be optimized along with process conditions that may vary depending on the amount recycled, to improve the cooking and/or washing effectiveness.

Optionally, the process may include co-combusting the recovered lignin with the low-ash biomass, to produce power. The recovered lignin may be combined with the low-ash biomass prior to combustion, or they may be co-fired as separate streams. When recovered lignin is combined with the low-ash biomass for making pellets, the lignin can act as a pellet binder.

In some embodiments, the fermentable hemicellulose sugars are recovered from solution, in solid form. In some embodiments, the fermentable hemicellulose sugars are fermented to produce of biochemicals or biofuels such as (but not limited to) ethanol, 1-butanol, isobutanol, acetic acid, lactic acid, or any other fermentation products. A purified fermentation product may be produced by distilling the fermentation product, which will also generate a distillation bottoms stream containing residual solids. A bottoms evaporation stage may be used, to produce residual solids.

Following fermentation, residual solids (such as distillation bottoms) may be recovered, or burned in solid or slurry form, or recycled to be combined into the biomass pellets. Use of the fermentation residual solids may require further removal of minerals.

Part or all of the residual solids may be co-combusted with the low-ash biomass, if desired. Alternatively, or additionally, the process may include recovering the residual solids as a fermentation co-product in solid, liquid, or slurry form. The fermentation co-product may be used as a fertilizer or fertilizer component, since it will typically be rich in potassium, nitrogen, and/or phosphorous.

In certain embodiments, the process further comprises combining, at a pH of about 4.8 to 10 or higher, a portion of the vaporized acetic acid with an alkali oxide, alkali hydroxide, alkali carbonate, and/or alkali bicarbonate, wherein the alkali is selected from the group consisting of potassium, sodium, magnesium, calcium, and combinations thereof, to convert the portion of the vaporized acetic acid to an alkaline acetate. The alkaline acetate may be recovered. If desired, purified acetic acid may be generated from the alkaline acetate.

The low-ash biomass has lower inorganic emissions potential compared to the original cellulosic biomass, in preferred embodiments. The reason is that the low-ash biomass will contain lower ash content compared to a process that does not extract inorganic components from the feedstock prior to combustion, in the manner disclosed herein.

Also, the low-ash biomass will generally have higher energy density compared to a process that does not extract hemicellulosic sugars from the feedstock prior to combustion. Depleting the biomass of hemicellulose sugars enriches the remaining material in lignin, which has a higher energy density than hemicellulose.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A process for producing low-ash biomass from cellulosic biomass, said process comprising:
   (a) providing a feedstock comprising cellulosic biomass;
   (b) providing an extraction solution comprising steam and/or hot water, and starting acetic acid;
   (c) treating said feedstock with said extraction solution under effective extraction conditions to produce an extract liquor containing soluble ash, hemicellulosic oligomers, acetic acid, dissolved lignin, and cellulose-rich solids;
   (d) separating at least a portion of said cellulose-rich solids from said extract liquor, to produce dewatered solids containing cellulose and lignin;
   (e) concentrating said extract liquor in an intermediate evaporation stage at a pH of 4.8 or less to release vaporized acetic acid, and recycling at least a portion of said vaporized acetic acid derived from said intermediate evaporation stage back to said extraction solution;
   (f) hydrolyzing said hemicellulosic oligomers contained in said extract liquor, under effective hydrolysis conditions, to produce hemicellulosic sugars, wherein said effective hydrolysis conditions release acetyl groups to generate additional acetic acid;
   (g) removing a vapor stream comprising water and vaporized acetic acid from said extract liquor in at least one evaporation stage at a pH of 4.8 or less, to produce a concentrated extract liquor comprising said hemicellulosic sugars;

(h) recycling at least a portion of said vapor stream from step (g), or a condensed form thereof, back to step (b) to provide at least some of said starting acetic acid for said extraction solution and to provide heat for step (c); and (i) drying said dewatered solids to produce said low-ash biomass.

2. The process of claim 1, wherein said extraction solution comprises steam in saturated, superheated, or supersaturated form.

3. The process of claim 1, wherein said extraction solution comprises hot water.

4. The process of claim 1, wherein said extraction solution contains from about 0.01 wt % to about 10 wt % acetic acid.

5. The process of claim 1, wherein said soluble ash includes one or more species selected from the group consisting of chlorine, chlorides, silica, silicates, metals, and combinations or derivatives thereof.

6. The process of claim 1, wherein said effective hydrolysis conditions in step (f) include hydrolysis in the presence of heat and acetic acid.

7. The process of claim 1, wherein said at least one evaporation stage in step (g) is controlled at a pH selected from about 3 to 4.8.

8. The process of claim 1, wherein said low-ash biomass contains about the same moisture content as contained in said cellulosic biomass.

9. The process of claim 1, wherein said low-ash biomass has higher energy density than said cellulosic biomass.

10. The process of claim 1, wherein said low-ash biomass has lower inorganic emissions potential compared to said cellulosic biomass.

11. The process of claim 1, said process further comprising combusting said low-ash biomass, to produce power.

12. The process of claim 11, said process further comprising co-combusting lignin with said low-ash biomass, to produce power.

13. The process of claim 1, said process comprising pelletizing said dewatered solids, optionally with lignin as a binder.

14. The process of claim 1, said process comprising pelletizing said low-ash biomass, optionally with lignin as a binder.

15. The process of claim 1, said process further comprising a step of fermenting said hemicellulosic sugars to a fermentation product.

16. The process of claim 15, said process further comprising distilling said fermentation product to produce a purified fermentation product and a distillation bottoms stream; introducing said distillation bottoms stream to a bottoms evaporation stage, to produce residual solids; and then co-combusting at least a portion of said residual solids with said low-ash biomass, to produce power.

17. The process of claim 15, said process further comprising distilling said fermentation product to produce a purified fermentation product and a distillation bottoms stream; introducing said distillation bottoms stream to a bottoms evaporation stage, to produce residual solids; and then recovering said residual solids as a fermentation co-product in solid, liquid, or slurry form for use as a fertilizer or fertilizer component.

18. A process for producing biomass pellets from cellulosic biomass, said process comprising:

(a) providing a feedstock comprising cellulosic biomass;

(b) providing an extraction solution comprising steam and/or hot water, and starting acetic acid;

(c) treating said feedstock with said extraction solution under effective extraction conditions to produce an extract liquor containing soluble ash, hemicellulosic oligomers, acetic acid, dissolved lignin, and cellulose-rich solids;

(d) separating at least a portion of said cellulose-rich solids from said extract liquor, to produce dewatered solids containing cellulose and lignin;

(e) concentrating said extract liquor in an intermediate evaporation stage at a pH of 4.8 or less to release vaporized acetic acid, and recycling at least a portion of said vaporized acetic acid derived from said intermediate evaporation stage back to said extraction solution;

(f) hydrolyzing said hemicellulosic oligomers contained in said extract liquor, under effective hydrolysis conditions, to produce hemicellulosic sugars, wherein said effective hydrolysis conditions release acetyl groups to generate additional acetic acid;

(g) removing a vapor stream comprising water and vaporized acetic acid from said extract liquor in at least one evaporation stage at a pH of 4.8 or less, to produce a concentrated extract liquor comprising said hemicellulosic sugars;

(h) recycling at least a portion of said vapor stream from step (g), or a condensed form thereof, back to step (b) to provide at least some of said starting acetic acid for said extraction solution and to provide heat for step (c); and (i) pelletizing said dewatered solids, or a dried form thereof, to produce biomass pellets.

* * * * *